(12) United States Patent
MacFarlane

(10) Patent No.: US 8,667,699 B2
(45) Date of Patent: Mar. 11, 2014

(54) PILLOW SELECTION AND SLEEPER APPRAISAL

(75) Inventor: Andrew Robert MacFarlane, Lane Cove (AU)

(73) Assignee: Healthcare Alliance Pty. Limited, North Sydney (AU)

( * ) Notice: Subject to any disclaimer, the term of this patent is extended or adjusted under 35 U.S.C. 154(b) by 243 days.

(21) Appl. No.: 13/234,317

(22) Filed: Sep. 16, 2011

(65) Prior Publication Data

US 2012/0005911 A1     Jan. 12, 2012

Related U.S. Application Data

(63) Continuation-in-part of application No. 11/915,092, filed as application No. PCT/AU2006/000676 on May 23, 2006, now Pat. No. 8,033,030.

(30) Foreign Application Priority Data

May 23, 2005     (AU) ................................ 2005902618

(51) Int. Cl.
  *A47G 9/00*       (2006.01)
  *A61B 5/103*      (2006.01)
(52) U.S. Cl.
  USPC ................................. 33/512; 5/636
(58) Field of Classification Search
  USPC ................................. 33/512; 5/636
  See application file for complete search history.

(56) References Cited

U.S. PATENT DOCUMENTS

| | | | | |
|---|---|---|---|---|
| 4,756,090 A * | 7/1988 | Pedrow | ........................... | 33/512 |
| 4,780,920 A * | 11/1988 | White | ............................... | 5/636 |
| 4,996,734 A * | 3/1991 | Rowe | ................................ | 5/636 |
| 5,457,832 A * | 10/1995 | Tatum | .............................. | 5/636 |
| 6,585,328 B1 * | 7/2003 | Oexman et al. | ............... | 700/117 |
| 7,203,983 B1 * | 4/2007 | Reeves et al. | ..................... | 5/636 |
| 7,546,651 B2 * | 6/2009 | Groteke et al. | ................... | 5/636 |
| 8,033,030 B2 * | 10/2011 | MacFarlane | .................... | 33/512 |
| 2006/0236460 A1 * | 10/2006 | Hooper | ............................. | 5/636 |
| 2007/0086947 A1 * | 4/2007 | Boyd | ............................. | 424/9.2 |
| 2008/0216242 A1 * | 9/2008 | Reeves | ............................. | 5/636 |
| 2009/0188043 A1 * | 7/2009 | Kirch | ............................... | 5/643 |
| 2012/0073057 A1 * | 3/2012 | Sramek | ............................. | 5/645 |

* cited by examiner

*Primary Examiner* — Christopher Fulton
(74) *Attorney, Agent, or Firm* — Design IP

(57) ABSTRACT

A neck measurement device (20) and a method of selecting a pillow (1, 41, 51) which takes into account the physique of the user are disclosed. A neck compression index (NCi) is calculated being the weight of the sleeper in kilograms divided by the shoulder width (ear to outer arm dimension) of the sleeper in centimeters. Preferably a compensated NCi is calculated which takes into account the softness or hardness of the mattress. A pillow resiliency is then selected based on the (compensated) NCi. Color coded pillow slips can be used to assist sleepers to self-select a pillow appropriate for their physique. Mail order and Internet based selling methods are disclosed.

14 Claims, 5 Drawing Sheets

PILLOW SELECTION AND SLEEPER APPRAISAL

CROSS REFERENCE TO RELATED APPLICATIONS

This application is a Continuation-in-part of U.S. patent application Ser. No. 11/915,092, filed Nov. 20, 2007, now issued as U.S. Pat. No. 8,033,030, which is a 371 of PCT International Application No. PCT/AU06/000676 filed May 23, 2006, which claims priority from Australian Patent Application No. 2005902618 filed May 23, 2005.

BACKGROUND ART

Many different types of pillows are manufactured and their properties vary considerably according to factors which as the shape of the pillow, the material from which the pillow is fabricated, the resiliency of that material, the age of the pillow, and so on. Similarly, there are many variations in mattresses each of which results from a different manufacturing technique, different materials, different resiliency and so on.

Since persons come in many different shapes, sizes, and weights, inevitably there will be many mismatches between sleepers, pillows and mattresses. In particular, poor pillow support is thought to require the neck muscles to partially support the head during sleep. As these neck muscles tire, the sleeper tosses and turns in order to provide some respite for the neck muscles but thereby disturbs their sleep.

The genesis of the present invention is a desire to substantially overcome, or at least ameliorate, the abovementioned difficulties by the provision of a pillow selection process and apparatus which takes into account the physique of the user and type of bed and/or mattress (e.g., slats, spring mattress, foam mattress, latex mattress, etc.).

FIELD OF THE INVENTION

The present invention relates to pillows and, in particular, to the selection of the correct pillow characteristics to suit the physique of the user and the bed on which the user sleeps.

SUMMARY OF THE INVENTION

In accordance with a first aspect of the present invention there is disclosed a neck measuring device for pillow selection, said device comprising a generally planar body having at least one corner defined by two substantially straight edges which are substantially perpendicular to each other, one surface of said body having a scale extending along one of said edges and having regularly spaced marked indicia extending along said scale, wherein said indicia are mirror reversed whereby a user standing in front of a mirror and holding said device to his shoulder and neck, can read said indicia in said mirror.

In accordance with a second aspect of the present invention there is disclosed a method of selecting a pillow to suit the physique of a user, said method comprising the steps of:
 (i) ascertaining the width of a shoulder of said user,
 (ii) ascertaining the weight of said user,
 (ii) from the results of steps (i) and (ii) calculating a neck compression index comprising the user's weight divided by their shoulder width,
 (iv) for each calculated neck compression index selecting a corresponding pillow.

BRIEF DESCRIPTION OF THE DRAWINGS

A preferred embodiment of the present invention will now be described with reference to the drawings in which.

DETAILED DESCRIPTION OF THE PREFERRED EMBODIMENTS

Figure 1:
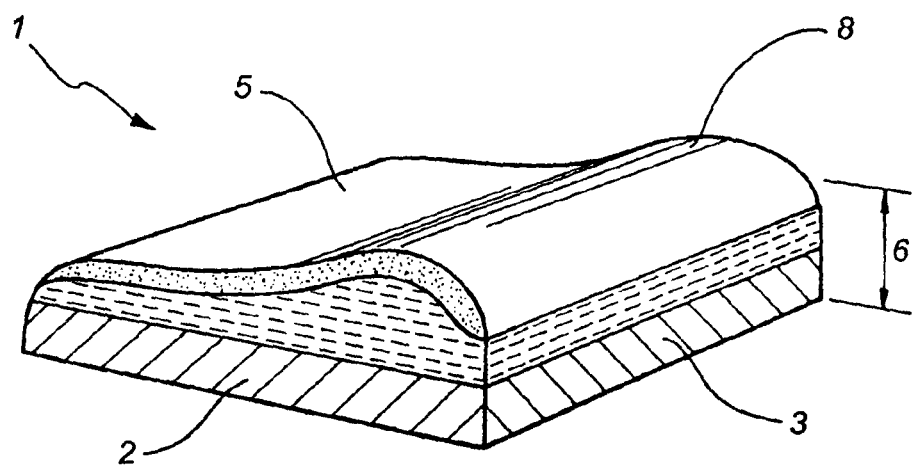
FIG. 1 is a schematic perspective view of a pillow in accordance with a preferred embodiment.

The pillow 1 of the preferred embodiment as illustrated in FIG. 1 has a longitudinal side 2 and a transverse side 3 (the other longitudinal side and the other transverse side not being apparent in FIG. 1). The upper surface 5 of the pillow 1 is shaped such that the longitudinal cross-section of the pillow is substantially constant. The transverse side 3 is preferably approximately 330 mm long and has an appreciable vertical extent 6 (unlike conventional pillows which have negligible vertical extent at their transverse side).

In addition, the upper surface 5 is formed with a crest 8 which is located closely adjacent the transverse side 3. Moving away from the crest 8 in a longitudinal direction towards the other transverse side, the upper surface 5 falls away. The longitudinal side 2 is approximately 590 mm in length and substantially vertical. The longitudinal side 2 has substantially the same appearance as any longitudinal cross-section through the pillow 1. This is in marked contrast to conventional pillows where the longitudinal sides are substantially merely an edge.

Preferably the pillow 1 is formed from two, or even three, layers of foamed plastics or other elastomeric materials, such as polyurethane or latex, which preferably have different densities.

Figure 2:
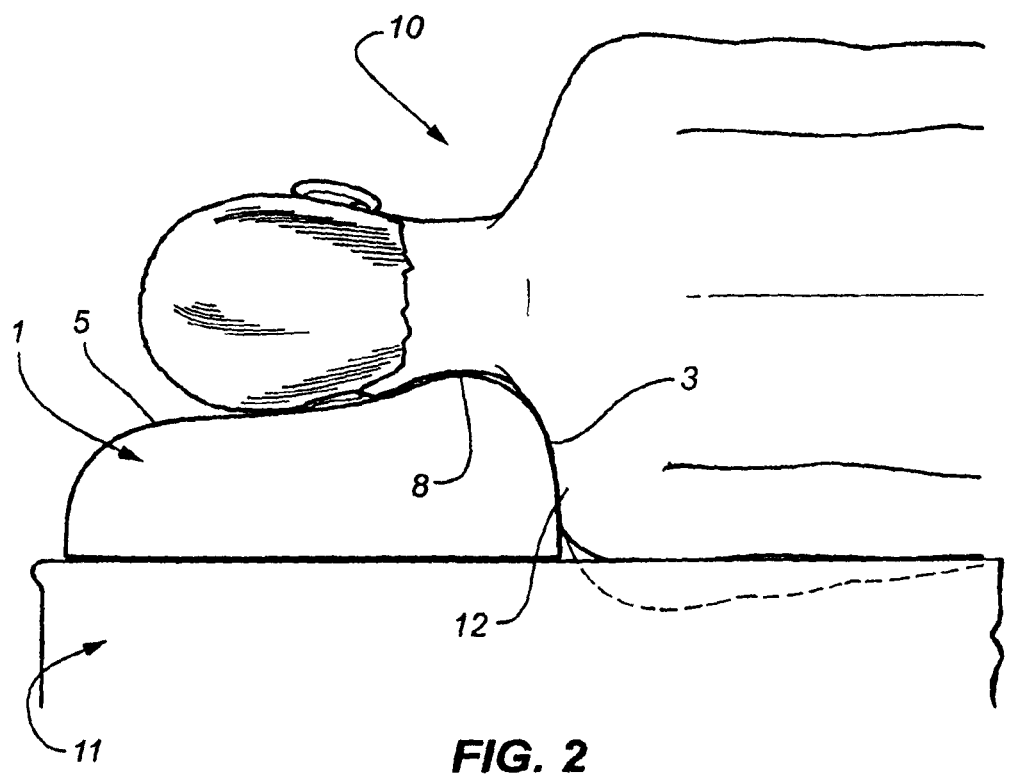
FIG. 2 is a schematic side elevation of a bed illustrating a sleeper sleeping on his side and utilizing the pillow of FIG. 1.

As seen in FIG. 2, a user 10 is depicted sleeping on a mattress 11 having a surface of negligible resilience or "give" and is also depicted sleeping on his side. It will be seen that the lower shoulder 12 of the user 10 either abuts, or is closely adjacent to, the transverse side 3. The crest 8 supports the neck of the user, in particular in the region between the ear and the shoulder. The upper portion of the head, in particular above the ear, is supported by the sloping surface of the pillow 1 which faces away from the shoulder 12.

An important advantage obtained by the pillow 1 is that the crest 8, in particular, supports the neck and lower head and thus the neck muscles are, in large part, relieved of this obligation. In addition, as indicated by broken lines in FIG. 2, the lower shoulder 12 in practice at least to some extent, sinks into the mattress 11 or other supporting surface of the bed on which the user is sleeping. It is also desirable to gauge the resilience or firmness of the mattress so that this can be taken into account in assessing the effective vertical depth of the shoulder 12 in the sleeping position illustrated in FIG. 2.

Figure 3:
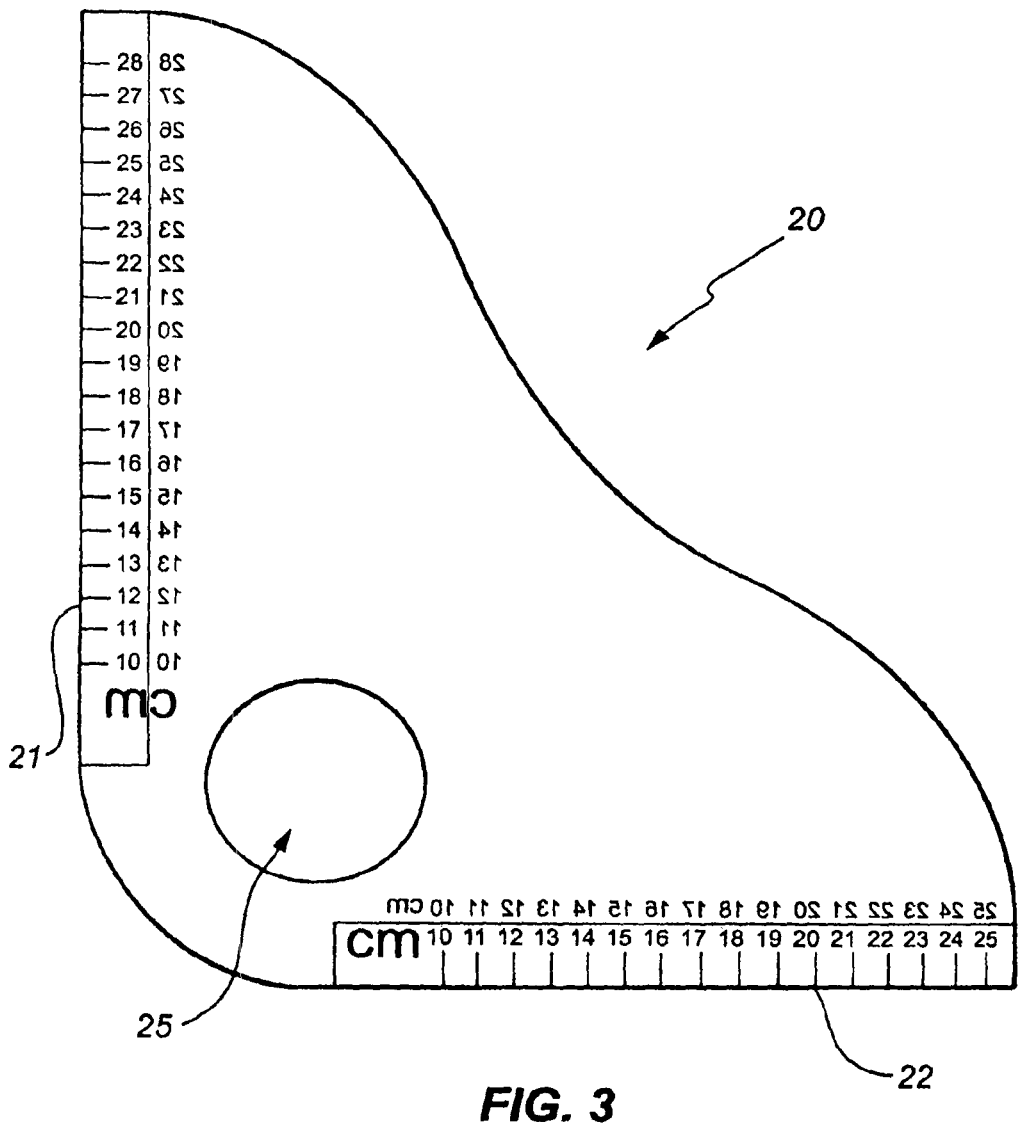
FIG. 3 is a plan view of a measuring device able to be utilized by a prospective purchaser.

In order to assist the user 2 to carry out the requisite measurements on himself, a generally L-shaped measuring device 20 as illustrated in FIG. 3 is provided. The device 20 has first and second edges 21, 22 which are substantially mutually perpendicular and each of which is provided with a ruled scale, preferably having two series of indicia. The first series of indicia is a conventional numerical scale and the second series of indicia is a mirror image reversal of the numbers of that scale. As a consequence of the mirror image reversal of the numbers of the scale, a user 10 can utilize the device 20 himself by standing in front of a mirror in order to measure the height of his head above the shoulder, and the horizontal extent from neck to shoulder. The shoulder width is the horizontal dimension from the user's ear to the outside edge of the adjacent arm. The head height is the vertical dimension from the upper surface of the shoulder to the top of the head. By looking in the mirror, the mirror reversed numerals are again reversed and thus are readily legible to the user 10.

Preferably the device 20 in addition to including instructions also includes an orifice 25 through which the user 10 may insert a thumb, for example, in order to assist the holding of the device 20 on the user's shoulder in order to take the requisite measurements. The device 20 is preferably fabricated from cardboard and has the scale, numbers and instructions printed thereon.

Figure 4:
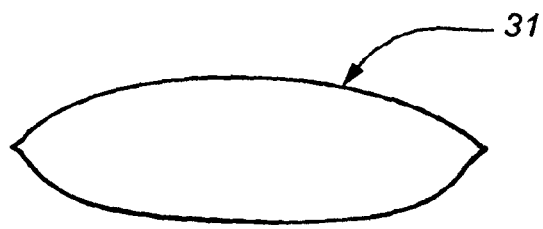
FIG. 4 is a longitudinal cross-section (i.e. in the long dimension of the bed) through a conventional pillow.
Figure 5:
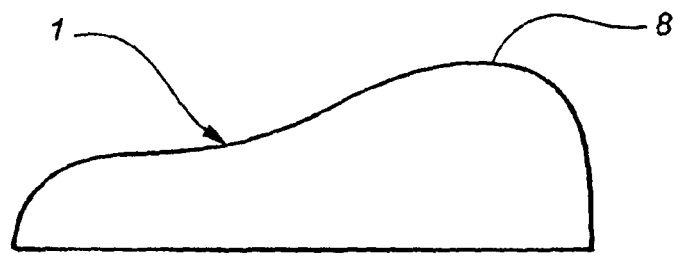
FIG. 5 is a longitudinal cross-section through the pillow of FIGS. 1 and 2.
Figure 6:
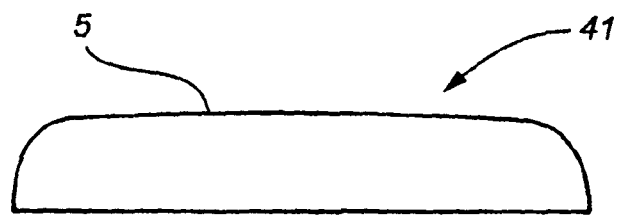
FIG. 6 is a longitudinal cross-section through a pillow most suitable for habitual back sleepers.
Figure 7:
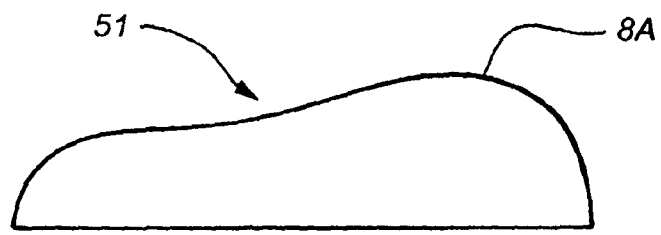
FIG. 7 is a longitudinal cross-section through a pillow most suitable for those sleepers who alternate between sleeping on their side and sleeping on their back.

Turning now to FIGS. 4-7, a number of different pillows are illustrated in longitudinal cross-section. FIG. 4 shows a conventional pillow 31 which has narrow transverse edges. FIG. 5 essentially repeats the shape of FIGS. 1 and 2 and illustrates the shape of the pillow 1 suitable for persons who habitually sleep on their side. FIG. 6 shows the shape of a pillow 41 suitable for a person who habitually sleeps on their back. It will be seen that the crest 8 is essentially reduced or abolished giving a generally level upper surface 5. For those persons who sleep alternatively on their back and on their side, a pillow 51 of the shape illustrated in FIG. 7 is best with a lesser crest 8A than the crest 8 of FIG. 5.

The inventor has observed that head size, and hence head weight, differs little from one individual to another, but that body size including shoulder width, and hence the weight which compresses the mattress 11, varies to a very substantially degree from one individual to another. In response to this observation the inventor has developed a Neck Compression index (hereinafter "NCi") which is the total weight of a person in kg divided by the width (or sideways extent) of the person's shoulder in centimeters. Thus a first person weighing 110 kg and having a slight build with a shoulder width of only 18 cms has a neck NCi of 110/18=6.1. Similarly another person who weighs 95 kg and has a normal build with a shoulder width of 18 cm has an NCi of 5.28. Conversely a 55 kg person with a shoulder width of 13 cms would have an NCi of 4.23. Typically the NCi is normally between about 3 and about 8.

The NCi provides an indication of the degree of pressure or force to which the pillow is subjected during sleep. The lower the NCi the less the density and/or hardness of the pillow which best matches the user's physique.

A very small percentage of the human population has either very long necks or very "tall" heads (or both) and thus need a pillow which is lengthened in the head to toe sleeping direction. The advantage of measuring the head height by the device 20 of FIG. 20 is that it enables this small percentage of the population to be accorded the different treatment they require.

The nature of the mattress is also preferably taken into account. For example, a very soft mattress compresses under the weight of the sleeper to an appreciable extent below the undeformed upper level of the mattress, for example by as much as 15 cm. Therefore before the neck compression index is calculated the shoulder width should be adjusted to account for the nature of the mattress. Furthermore, a pillow top (an additional layer of padding) can reduce the shoulder width by from 2-5 cms. These adjustments are summarized in the following table.

TABLE 1

| Mattress Type | Adjustment to measured shoulder width |
| --- | --- |
| Hard | Subtract 2 cm |
| Medium | Subtract 2-5 cm |
| Soft | Subtract 5-8 cm |
| Pillow Top | Subtract 2-5 cm |

That is, using the adjusted shoulder width an NCi can be calculated which is compensated for the nature of the mattress (and also any pillow top).

Turning now to the pillow, different manufacturing techniques have different ways of measuring the resilience of the pillow. For latex pillows there is a standard referred to as "indent deflection loading" (hereinafter "IDL") which utilizes the pressure or weight required to compress by 40% a block of foam typically one foot by one foot in area to be compressed and eight inches thick. Very soft latex or foam pillows which compress to a substantial degree have an IDL of typically 6-8 whereas "hard" latex or foam pillows which only compress a small amount have an IDL of typically 10-15.

Pillows made from polyurethane foam, or latex, use a different measuring criterion, namely the mass or density of the foam material expressed in kilograms per cubic meter. "Soft" pillows are typically 50-65 kg/m$^3$ whilst "hard" pillows are typically 70-75 kg/m$^3$.

In addition, pillows made from polyurethane or latex foam use a still further standard rating which utilizes two letters and a pair of two digit numbers. "Soft" foam pillows have a rating such as VF52-40, or OP35-110 or HF18-35 whereas "hard" foam pillows have a rating such as AA15-60, or AA17-80 or LR38-40. These figures need to be modified somewhat if the pillow is provided with an array of vertical holes (e.g. 5 mm in diameter) and/or horizontal channels, both of which reduce the effective hardness.

With the above in mind it is possible to draw up a selection table which enables a pillow to be selected once the neck compression index, and preferably the compensated neck compression index, has been calculated. Table II is such a selection table.

TABLE II

| Compensated NCi Range | Latex Pillow IDL Range | Latex Pillow kg/m$^3$ range | Foam Pillow Hardness & Density Grade |
| --- | --- | --- | --- |
| 3-4 | 8-9 | 50-60 | HS18-35 |
| 4-5 | 9-10 | 65 | VF52-40 |
| 5-6 | 10-12 | 70 | ST29-60; LR38-40 |
| 6-8 | 12-15 | 75 | MA25-60; AA17-80; AA15-60 |

A preferred embodiment of the present invention is particularly applicable to accommodation establishments such as hotels, motels, and the like. Such establishments pride themselves on offering their customers a good night's sleep which naturally requires that the customer, mattress and pillow be matched to the maximum possible extent. This can be achieved in accordance with the preferred embodiment as follows.

The accommodation establishment normally has a single type (or a restricted number of types) of mattress throughout all its bedrooms. Thus the establishment can select, say, four different types of pillows which cover the expected range of uncompensated neck compression indices for substantially all their customers. These pillows are then placed in corresponding color coded pillow slips and all four types of pillows are provided for each bed in each room. In addition, each room is provided with the device of FIG. 3 and instructions (labeled Personal Pillow Selection) to the room occupant to use the device of FIG. 3 to measure his NCi. Once this has been calculated it falls within one of the ranges of pillows and so the correspondingly colored pillow slip is determined and the correct pillow thereby selected. The uncompensated NCi can be used because the nature of the mattress is known beforehand.

In another embodiment, a mail order pillow purchasing business can be conducted in which the customers using a personal measuring kit determine their weight and their neck and head dimensions and supply these together with their details of their mattress to the vendor. The vendor then calculates the compensated NCi and determines a suitable pillow which is then either fabricated or selected from the range of pillows on offer by different pillow manufacturers.

Figure 8:
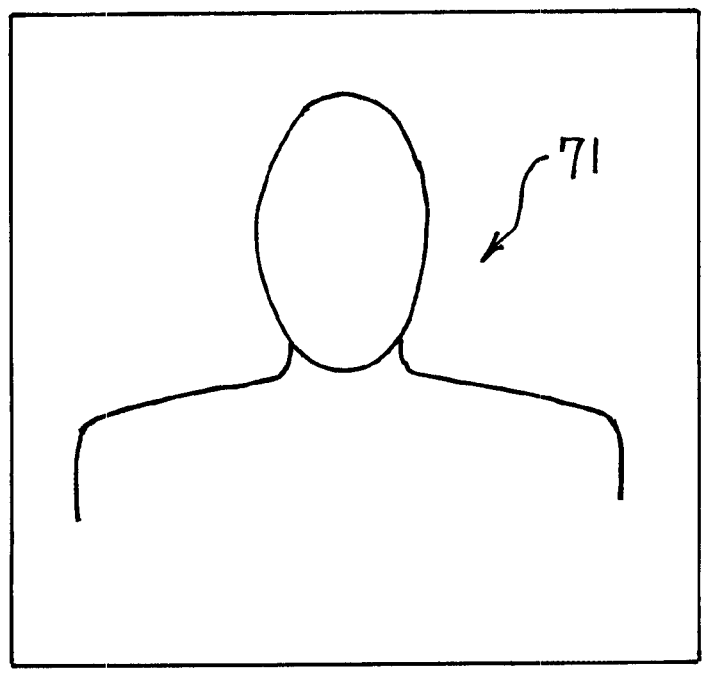
FIG. 8 is a schematic representation of a passport style photograph of a purchaser utilizing a website based pillow purchasing system.
Figure 9:
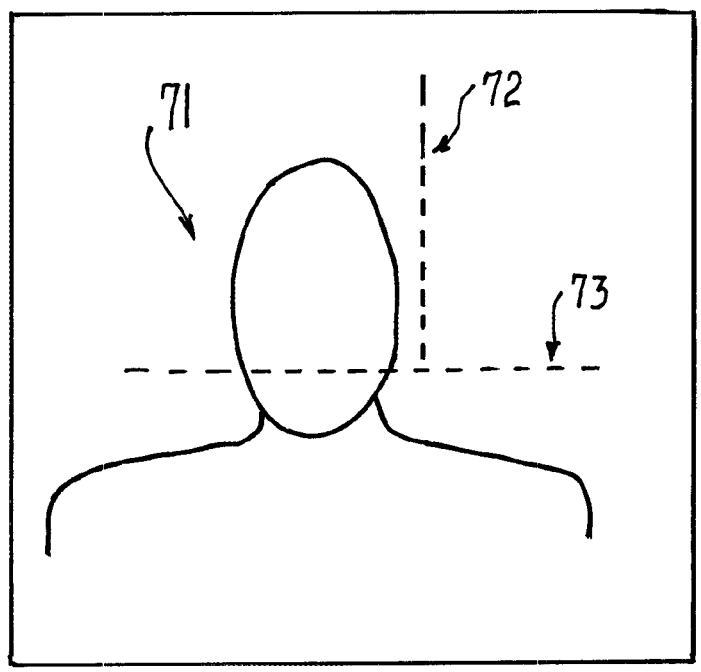
FIG. 9 is a representation of the photograph of FIG. 8 after it has been uploaded by the purchaser to the vendor's website.
Figure 10:
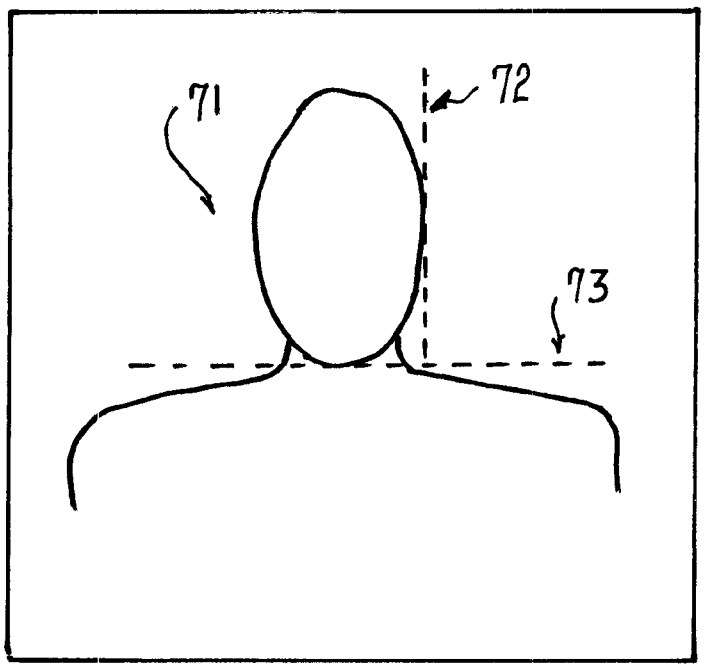
FIG. 10 is a representation similar to FIG. 9 but illustrating the photograph aligned with an internal template.

In a still further embodiment, the mail-order pillow purchasing business can be conducted via a website and the Internet. In particular, in this embodiment the device of FIG. 3 is not required to be utilized by the prospective purchaser. Instead, to ascertain the width of the purchaser's shoulder, the purchaser uses a conventional webcam (or camera able to take a photograph and send it via the Internet to a distant destination) to take a head and shoulders photograph 71 (similar to a passport photograph) of themselves as illustrated in FIG. 8. The photograph 71 is then transmitted to the website of the vendor and appears to the purchaser as illustrated in FIG. 9. The purchaser is then able to translate his image relative to two intersecting markers 72, 73 illustrated by dashed lines in FIG. 9, thereby resulting in the situation as illustrated in FIG. 10. Here the purchaser's left ear is aligned with the vertical marker 72, and the top of the shoulders are aligned with the horizontal marker 73. This establishes the purchaser's photograph in relation to a template stored in the computer which operates the vendor's website.

Figure 11:
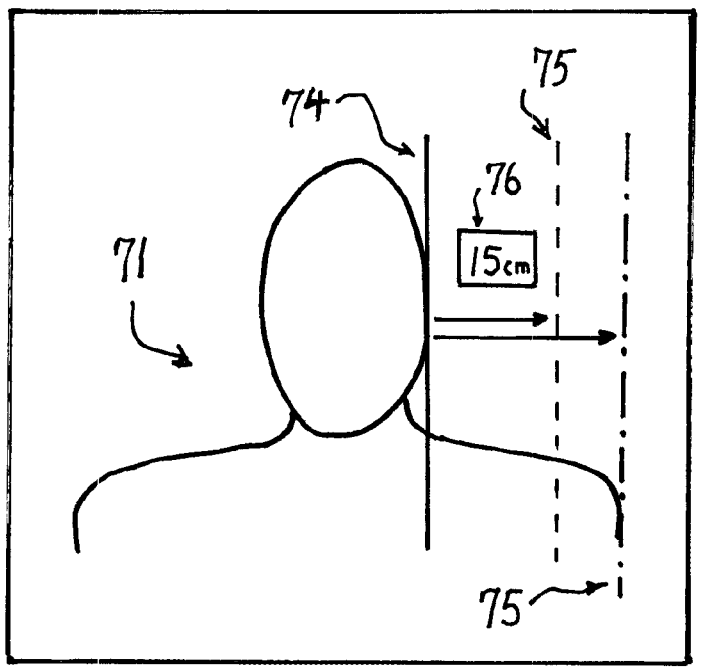
FIG. 11 is a representation of the way in which the shoulder width of the purchaser is ascertained.

Next the vendor displays on the screen, a marker line 75 indicating the horizontal distance to the right of a baseline 74 aligned with the purchaser's left ear (as seen in FIG. 11), the marker line 75 initially being illustrated by a broken line. Associated with the marker line 75 is a screen display 76 which displays a distance in centimeters which represents the length of the arrow extending from the baseline 74 to the marker line 75. Initially this distance in centimeters is, say, 15 cm.

The purchaser then moves the marker line to the right as seen in FIG. 11 so that the marker line 75 is flush with the left shoulder of the purchaser as indicated by a dot-dash line in FIG. 11. This causes the screen display 76 to increase to, say, 18 cm which is the width of the purchaser's shoulder which is then either manually or automatically entered into the data being collected by the vendor and from which the neck compression index is to be calculated.

As mentioned previously, the inventor has observed that head size differs little from one individual to another. This is supported by anthropometry studies such as those conducted amongst British navy personnel and reported in the book "The Measure of a Man and a Woman" published in 2002. Consequently, it is known that for, say 99% of purchasers, the length of the neck and head is the same and is approximately 27-28 cm. Since the scale on the photograph is the same in the vertical direction as in the horizontal direction, an assumed head height of 27.5 cm enables the distance of the marker line 75 from the baseline 74 to be calculated with acceptable accuracy, and displayed in the screen display 76. Consequently, as the position of the marker line 75 is varied, so the calculated distance displayed in the screen display 76 is also varied, all based on the assumed height of the head and neck.

The foregoing describes only some embodiments of the present invention and modifications, obvious to those skilled in the art, can be made thereto without departing from the scope of the present invention.

In this specification, inferences to the masculine gender are to be taken to include the feminine gender, and vice versa.

The term "comprising" (and its grammatical variations) as used herein is used in the inclusive sense of "having" or "including" and not in the exclusive sense of "consisting only of".

While the principles of the invention have been described above in connection with preferred embodiments, it is to be clearly understood that this description is made only by way of example and not as a limitation of the scope of the invention.

The invention claimed is:

1. A method of selecting a pillow to suit the physique of a user, said method comprising the steps of:
   (i) ascertaining the width of a shoulder of said user,
   (ii) ascertaining the weight of said user,
   (iii) from the results of steps (i) and (ii) calculating a neck compression index comprising the user's weight divided by their shoulder width,
   (iv) for each calculated neck compression index selecting a corresponding pillow.

2. The method as claimed in claim 1 including the further step of:
   (v) enclosing different pillows within different pillow slips whereby step (iv) comprises selecting a different pillow slip.

3. The method as claimed in claim 2 including the further step of:
   (vi) arranging for each of said different pillow slips to be a different colour.

4. The method as claimed in claim 1 including the step of:
   (vii) using a neck measuring device for pillow selection, said device comprising a generally planar body having at least one corner defined by two substantially straight edges which are substantially perpendicular to each other, one surface of said body having a scale extending along one of said edges and having regularly spaced marked indicia extending along said scale, wherein said indicia are mirror reversed whereby a user standing in front of a mirror and holding said device to his shoulder and neck, can read said indicia in said mirror in carrying out step (i).

5. The method as claimed in claim 1 and carried out by a guest of an accommodation establishment in accordance with instructions provided by said accommodation establishment.

6. The method as claimed in claim 1 and carried out by a person visiting a website via a communications link.

7. The method as claimed in claim 6 wherein said communications link comprises the internet.

8. A method of selecting a pillow to suit the physique of a user, said method comprising the steps of:
(i) ascertaining the width of a shoulder of said user,
(ii) ascertaining the weight of said user,
(iii) from the results of steps (i) and (ii) calculating a neck compression index comprising the user's weight divided by their shoulder width,
(iv) for each calculated neck compression index selecting a corresponding pillow, and
(v) modifying step (i) to calculate an adjusted shoulder width taking into account the nature of the mattress to result in a compensated neck compression index.

9. The method as claimed in claim 8 including the further step of:
(vi) enclosing different pillows within different pillow slips whereby step (iv) comprises selecting a different pillow slip.

10. The method as claimed in claim 9 including the further step of:
(vii) arranging for each of said different pillow slips to be a different colour.

11. The method as claimed in claim 8 including the step of:
(viii) using a neck measuring device for pillow selection in carrying out step (i), said device comprising a generally planar body having at least one corner defined by two substantially straight edges which are substantially perpendicular to each other, one surface of said body having a scale extending along one of said edges and having regularly spaced marked indicia extending along said scale, wherein said indicia are mirror reversed whereby a user standing in front of a mirror and holding said device to his shoulder and neck, can read said indicia in said mirror.

12. The method as claimed in claim 8 and carried out by a guest of an accommodation establishment in accordance with instructions provided by said accommodation establishment.

13. The method as claimed in claim 8 and carried out by a person visiting a website via a communications link.

14. The method as claimed in claim 13 wherein said communications link comprises the internet.

* * * * *